US00PP23896P2

(12) United States Plant Patent
Cho

(10) Patent No.: US PP23,896 P2
(45) Date of Patent: Sep. 10, 2013

(54) ***COLOCASIA* PLANT NAMED 'BLACK CORAL'**

(50) Latin Name: *Colocasia esculenta*
Varietal Denomination: Black Coral

(76) Inventor: John Cho, Paia, HI (US)

( * ) Notice: Subject to any disclaimer, the term of this patent is extended or adjusted under 35 U.S.C. 154(b) by 129 days.

(21) Appl. No.: 13/317,202

(22) Filed: Oct. 11, 2011

(51) Int. Cl.
*A01H 5/00* (2006.01)

(52) U.S. Cl.
USPC ..... Plt./373

(58) Field of Classification Search
USPC ..... Plt./373, 263.1
See application file for complete search history.

*Primary Examiner* — Howard Locker

(57) ABSTRACT

A new cultivar of *Colocasia* plant named 'BLACK CORAL' that is characterized by a combination of large dark purple to black leaves with a glossy finish and semi-glossy dark burgundy colored petioles. In combination these characteristics distinguish 'BLACK CORAL' from all other varieties of *Colocasia* known to the inventor.

4 Drawing Sheets

This invention was made with Government support under Grant No. 2005-31100-06015/HAW00948H awarded by the U.S. Department of Agriculture. The Government has certain rights in this invention.

Genus: *COLOCASIA.*
Species: *esculenta.*
Denomination: 'BLACK CORAL'.

BACKGROUND OF THE INVENTION

The present invention relates to a new and distinct variety of *Colocasia* commonly known as the taro plant or elephant ears. *Colocasia* is grown as a food crop or for use as an ornamental for container or the landscape. The new cultivar is known botanically as *Colocasia esculenta* and will be referred to hereinafter by the cultivar name 'BLACK CORAL'.

*Colocasia* is a tuberous rooted perennial which is native to tropical Asia and Polynesia. It grows to 1.5-2 m in height from starchy tubers. The leaves of *COLOCASIA* are heart-shaped and very large in size. The tuberous roots are cooked and eaten as a starchy staple in many tropical areas. It is also grown as ornamental plants for the landscape in warmer climates or as a container plant in colder areas.

The new *Colocasia* variety named 'BLACK CORAL' is the product of a formal breeding program of the University of Hawaii, Kula. The purpose of the breeding program was to develop new commercial varieties by combining attributes not found in currently commercially available varieties.

'BLACK CORAL' is a seedling selection from the controlled pollination between the female parent breeding line '2002-202' (unpatented) and male parent variety 'Diamond Head' (U.S. Plant Pat. No. 19,939). Initially designated as '2006-147', 'BLACK CORAL' was selected in 2006.

'BLACK CORAL' exhibits large dark purple almost black colored leaves with a glossy finish. 'BLACK CORAL' produces uniform dark burgundy colored petioles. 'BLACK CORAL' is similar in size to its female parent and has glossy dark purple to almost black leaves compared to its female parent whose leaves have a matte surface and are colored purple. 'BLACK CORAL' is similar in plant size, leaf color and glossy leaf to its male parent, 'Diamond Head'. However 'BLACK CORAL' exhibits an even darker, blacker leaf color with slightly bluish glossy venation. In addition, 'BLACK CORAL' exhibits prolific basal branching. In these aspects, this new variety differs from both of its parents.

The closest comparison variety known to the inventor is its male parent, 'Diamond Head' (U.S. Plant Pat. No. 19,939) as described and compared above.

The traditional means of asexual propagation of the genus *Colocasia* is the excision and replanting of a shoot which consists of the apical 1 cm-2 cm portion of the plant corm with the attached basal 15 cm-20 cm portion of the petiole. In regions of the world where *Colocasia* is grown, this plant shoot is known as a "huli", and the means of propagation is known as "huli propagation." Asexual propagation of hulis of 'BLACK CORAL' began in 2006 in Hawaii by the inventor using huli propagation whereby the apical shoots are separated from the plant by cutting the shoot at the top of the corm immediately above the newest leaf scar and planted. Evaluation in field studies have shown the unique features of 'BLACK CORAL' to be stable, uniform, and reproduces true to type in successive generations of asexual propagation.

SUMMARY OF THE INVENTION

The following traits have been repeatedly observed and represent the distinguishing characteristics of the new *Colocasia* variety named 'BLACK CORAL'. In combination these traits set 'BLACK CORAL' apart from all other varieties of *Colocasia* known to the inventor. 'BLACK CORAL' has not been tested under all possible conditions and phenotypic differences may be observed with variations in environmental, climatic and cultural conditions, however, without any variance in genotype:

1. 'BLACK CORAL' exhibits large saggitate-shaped leaves and slightly undulating margins.
2. The leaves of 'BLACK CORAL' are a dark purple to black in color with glossy bluish venation.
3. The surface of the leaves of 'BLACK CORAL' is glossy.
4. 'BLACK CORAL' has semi-glossy dark burgundy colored petioles.
5. 'BLACK CORAL' exhibits prolific basal branching.

BRIEF DESCRIPTION OF THE DRAWINGS

The accompanying color drawings

Figure 1:
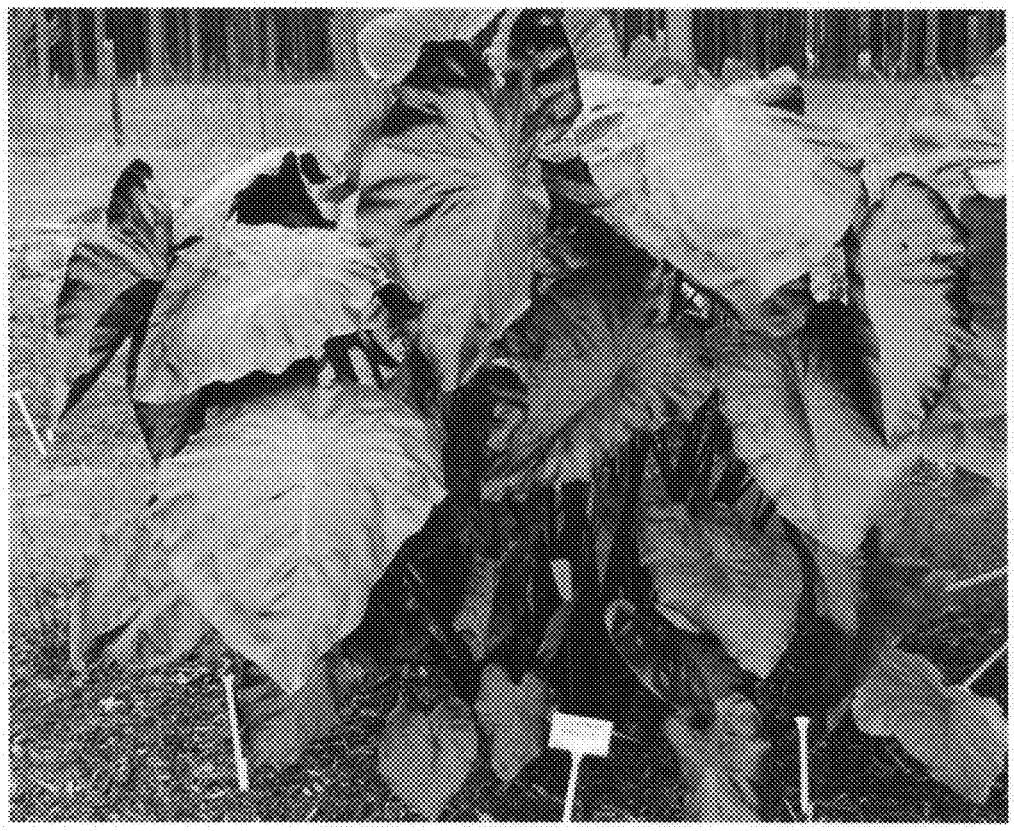
FIGS. 1 to 4 illustrate the overall appearance of 'BLACK CORAL' showing the colors as true as it is reasonably possible to obtain in colored reproductions of this type. Colors in the drawing may differ from the color values cited in the detailed botanical description, which accurately describe the actual colors of the new variety 'BLACK CORAL'.

The drawing labeled as FIG. 1 shows 'BLACK CORAL' grown from a huli after approximately 3 months.

Figure 2:
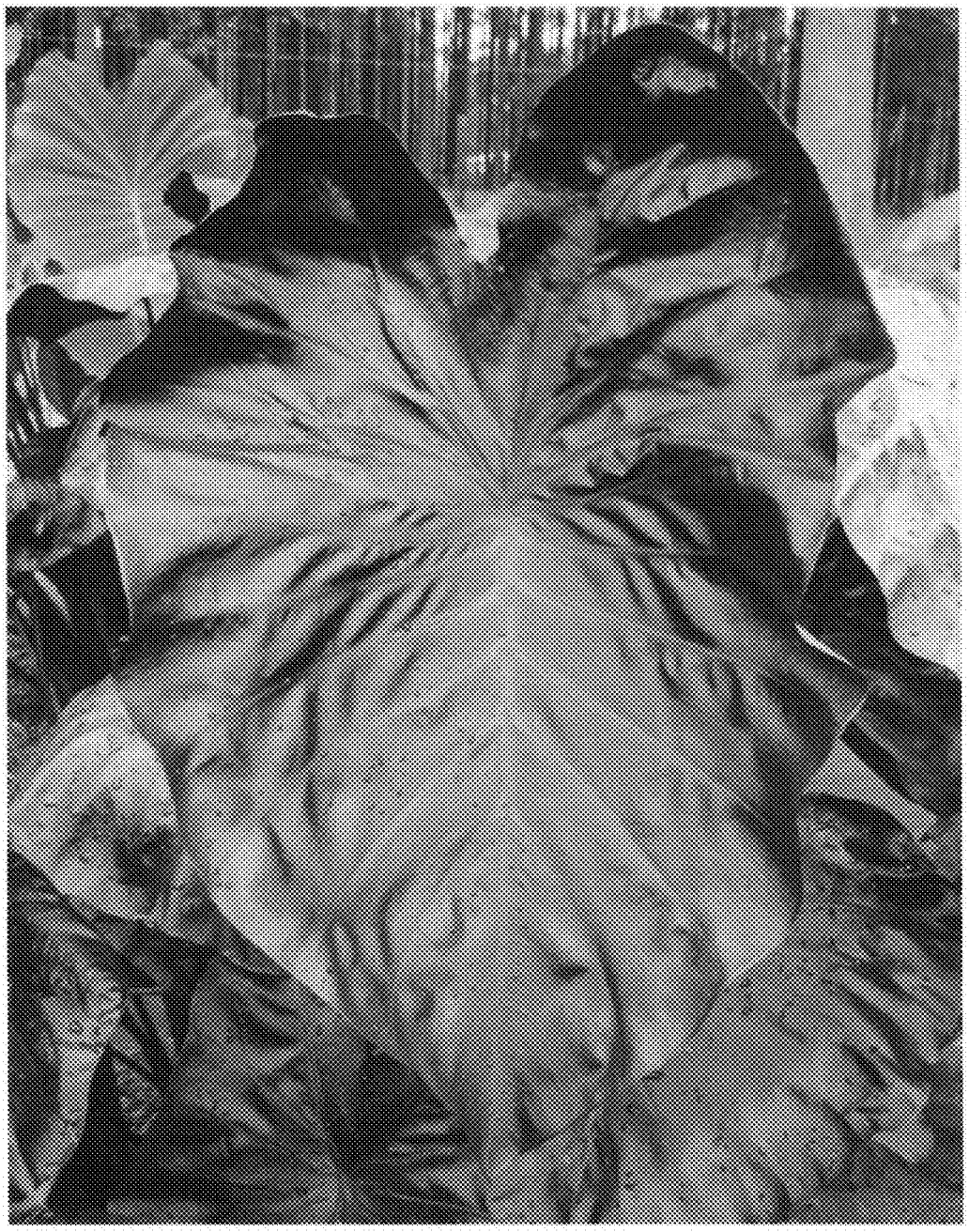

The drawing labeled FIG. 2 illustrates a sagittate 'BLACK CORAL' mature leaf blade. Lamina is dark purple to black with a glossy finish.

Figure 3:
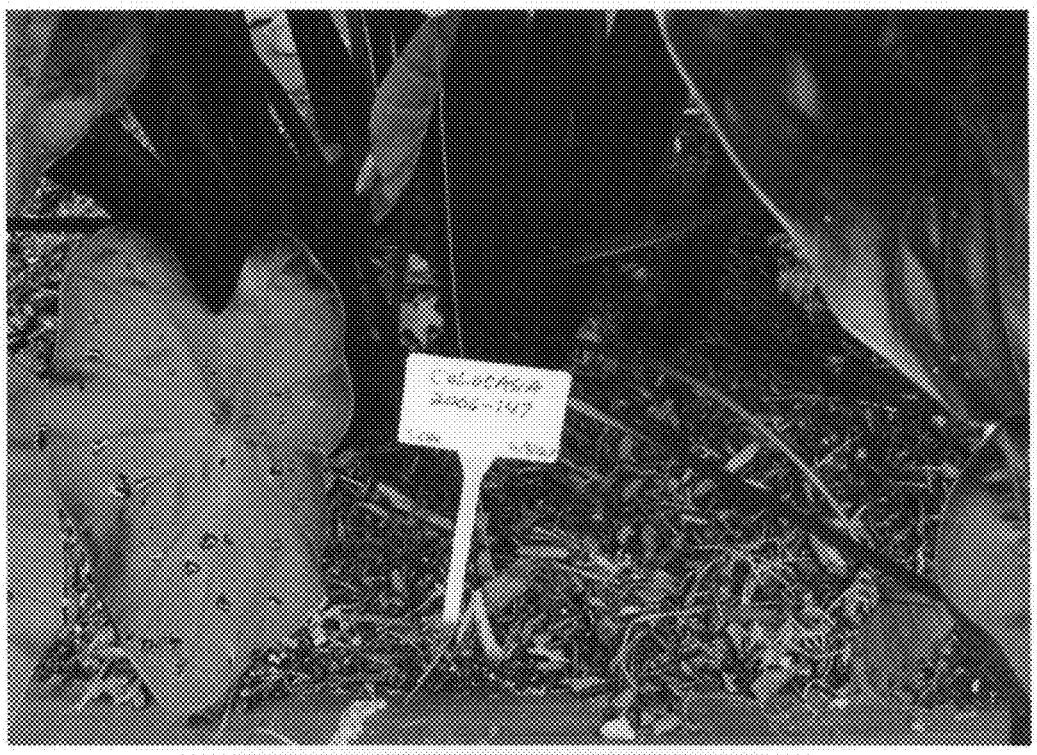

The drawing labeled as FIG. 3 shows the semi glossy burgundy to dark burgundy colored petioles of 'BLACK CORAL'.

Figure 4:
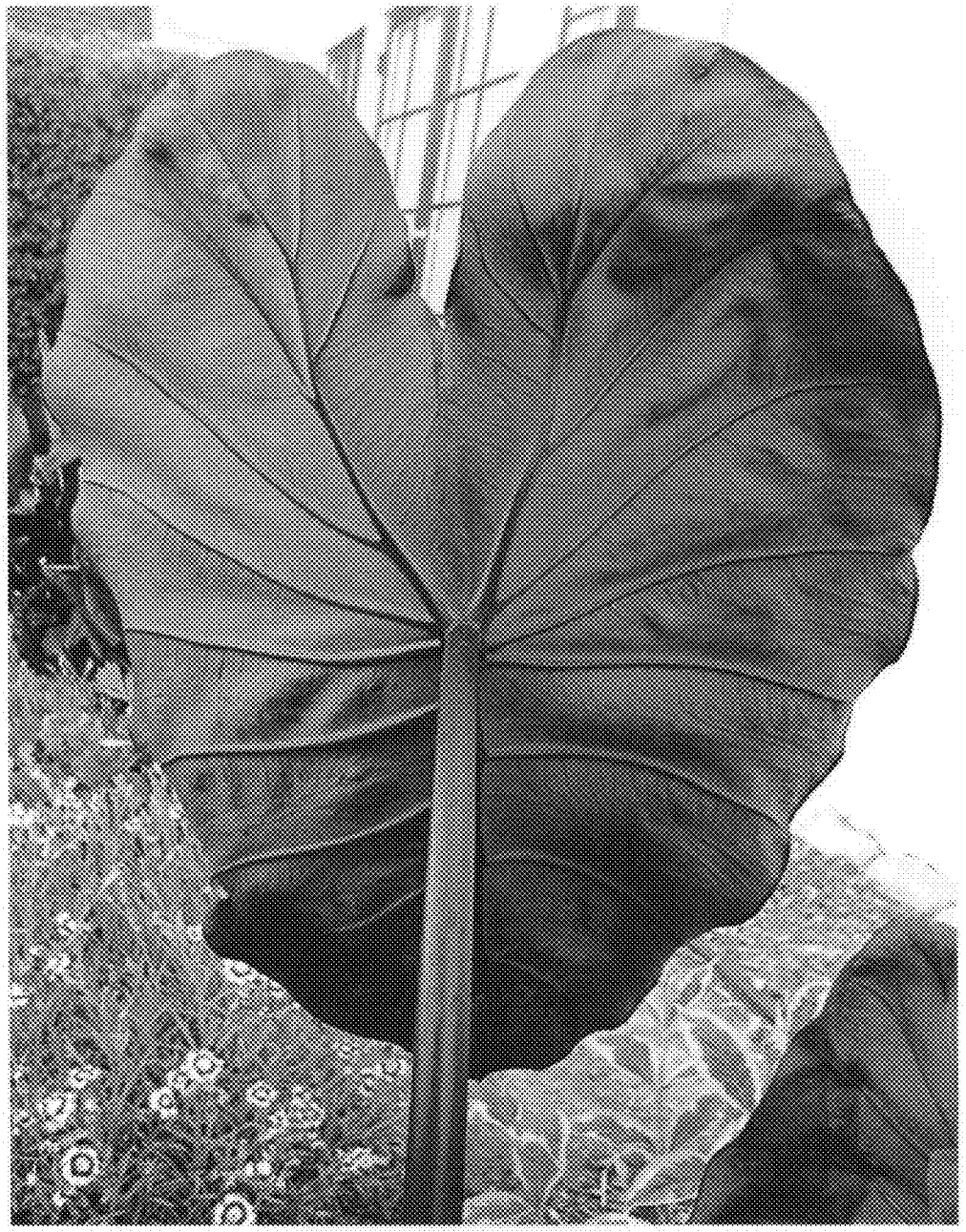

The drawing labeled as FIG. 4 shows the underside of a mature leaf of 'BLACK CORAL' with light purple lamina and burgundy venation.

All drawings have been made from plants which have been grown out-of-doors in Santa Barbara, Calif. No growth regulators have been applied.

BOTANICAL DESCRIPTION OF THE PLANT

The following is a detailed description of the new *Colocasia* plant named 'BLACK CORAL'. Data was collected from plants that were 12 months of age grown outside in Santa Barbara, Calif. The color determinations are in accordance with The 2007 edition of The Royal Horticultural Society Colour Chart, London, England, except where general color terms of ordinary dictionary significance are used. The growing requirements are similar to other *Colocasia*

Botanical classification:

Genus: *Colocasia.*

Species: *esculenta.*

Denomination: 'BLACK CORAL'.

Common name: Taro or elephant ears.

Plant use: Food, container or landscape plant.

Cultural requirements: Cultural requirements are well draining soil or growing media, full sun to partial shade.

Root system: Fibrous.

Plant vigor: Vigorous.

Plant growth rate:

Parentage:

*Female parent.*—'2002-202' (unpatented).

*Male parent.*—'Diamond Head' (U.S. Plant Pat. No. 19,939).

Plant description: The plant has 4 to 7 suckers closely attached to the mother plant. A "mother plant" is the plant material which is first introduced into the soil to begin production. Typically, this plant material contains part of the huli and 2-3 leaf blades. This produces a "mother corm" which produces lateral shoots called 'cormels' which give rise to daughter plants. Daughter plants begin to appear above soil level about 2-3 months after planting of the mother plant.

Plant dimensions (at one year of age): Height 1 m; width 1 m.

Plant hardiness: USDA Zone 7b.

Propagation: Propagation is accomplished by huli propagation and by tissue culture.

Propagation time (huli propagation): Daughter plants appear above soil around 2-3 months after planting.

Propagation time (tissue culture): If starting with clean stock (i.e. no virus present), plants are viable and rooted approximately three months after initiation.

Crop time: Between 8 and 10 weeks are required to produce a saleable 1 gallon plant from a rooted young plant at minimum temperature of 18° C., either in a heated greenhouse or outside in warm regions.

Pest or disease susceptibility and resistance: No more or less susceptible to disease or pests than other cultivars.

Foliage:

*Number.*—On average, a 5-6 month old mother plant maintains 6-8 functional leaves at a time; each new leaf is produced approximately every 10 days until the corm matures.

*Petioles.*—Length: Up to 75 cm in length. Width: 6 mm in diameter immediately below leaf attachment, increasing to 20 mm in diameter at emergence from sinus. Color: 187A. Sap color: Colorless.

*Leaf.*—Dimensions at maturity (5-6 months old): 355 mm in length and 235 mm in width. Aspect: Erect with apex down. Shape: Sagittate lamina. Margins: Entire. Apex: Pointed. Base: Peltate. Lamina appendages: Absent. Attachment: Petiolate with characteristic tissue formed at junction of leaf blade with the upper termination of the petiole. This area of the leaf tissue is also known as the "piko" and is evident by virtue of its upper surface being the same color as the veins or darker. The principal veins radiate from the piko. Piko color: 187A. Leaf sheaf: Open. Texture: Glossy. Leaf color (adaxial surface): Generally very dark blue, darker than 103A. Fully expanded leaves in full sun are black 203A. Leaf color (abaxial surface): N186A. Venation: Palmate. Veins: Three principal veins radiating from the piko with the largest a midrib extending from the piko to the tip of the lamina with up to 9 pairs of secondary veins radiating from it. Vein color (adaxial surface): Ranges between 103D to 103A, becoming entirely N186A on fully expanded leaf which is exposed to full sun. Vein color (abaxial surface): 187A.

Inflorescence and reproductive organs: The inflorescence arises from the leaf axils and is comprised of spathe borne on a short peduncle and containing a spadix.

*Peduncle.*—Dimensions: 31 cm in length, 7 mm-10 mm in diameter. Color: N187A.

*Spathe.*—Description: Large yellowish-purple bract, 178 mm long, which sheathes the spadix. The lower part of the spathe is dark purple (N187A) in color and wraps tightly around the spadix. The upper part of the spathe is yellow (13C) in color with dark purple (N187A) streaks and is rolled inward at the apex, but is open on one side to reveal the male flowers on the spadix. The upper and lower portions of the spadix are separated by a narrow neck region.

*Spadix (botanically, a spike) and flowers.*—Description: 70 mm to 73 mm in length with a fleshy central axis along which small sessile flowers arranged as follows: Female flowers are borne along the basal portion of the axis and are completely occluded from view. Sterile flowers are borne along the central portion of the axis towards and within the narrow neck of the spathe. Male flowers are borne along the upper portion of the axis, except for the apex which does not bear any flowers.

The invention claimed is:

1. A new and distinct cultivar of *Colocasia* plant named 'BLACK CORAL' as described and illustrated herein.

* * * * *